(12) United States Patent
Devarakonda et al.

(10) Patent No.: US 11,081,215 B2
(45) Date of Patent: Aug. 3, 2021

(54) MEDICAL RECORD PROBLEM LIST GENERATION

(71) Applicant: INTERNATIONAL BUSINESS MACHINES CORPORATION, Armonk, NY (US)

(72) Inventors: Murthy V. Devarakonda, Peekskill, NY (US); Safa Messaoud, Sfax (TN); Ching-Huei Tsou, Briarcliff Manor, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 706 days.

(21) Appl. No.: 15/611,144

(22) Filed: Jun. 1, 2017

(65) Prior Publication Data

US 2018/0349555 A1 Dec. 6, 2018

(51) Int. Cl.
*G06N 99/00* (2019.01)
*G16H 10/60* (2018.01)
(Continued)

(52) U.S. Cl.
CPC .......... *G16H 10/60* (2018.01); *G06N 3/0454* (2013.01); *G06N 5/003* (2013.01); *G06N 20/00* (2019.01);
(Continued)

(58) Field of Classification Search
CPC ........ G06F 19/345; G06F 17/30; G06F 15/18; G06Q 10/00; G06Q 50/00; G06N 7/00; G06N 5/02
(Continued)

(56) References Cited

U.S. PATENT DOCUMENTS 7,801,841 B2 * 9/2010 Mishra .................... G06F 40/30
706/55
7,899,764 B2 * 3/2011 Martin .................... G06F 19/00
706/12
(Continued)

FOREIGN PATENT DOCUMENTS

CN 102222153 A 10/2011
CN 105912846 A 8/2016
(Continued)

OTHER PUBLICATIONS

Google patents search, Nov. 25, 2019 (Year: 2019).*
(Continued)

*Primary Examiner* — Dilek B Cobanoglu
(74) *Attorney, Agent, or Firm* — Cantor Colburn LLP; Kristofer Haggerty

(57) ABSTRACT

Embodiments of the invention include methods, systems, and computer program products for generating a medical problem list. A non-limiting example of the method includes receiving, by a processor, a plurality of disease categories. A disease category set that includes a plurality of top level disease categories is defined using the processor, wherein the disease category set is based at least in part upon the plurality of disease categories. The processor is used to extract a plurality of candidate training problems from an electronic patient record training set. The processor is used to assign each of the candidate training problems to the plurality of top level disease categories. The processor is used to generate a disease category model for each of the top level disease categories from the electronic patient record training set using a machine learning technique.

13 Claims, 8 Drawing Sheets

(51) Int. Cl.
    *G16H 50/50*     (2018.01)
    *G06N 20/00*     (2019.01)
    *G06N 5/00*     (2006.01)
    *G06N 3/04*     (2006.01)
    *G16H 50/20*     (2018.01)
    *G16H 40/67*     (2018.01)
    *G16H 50/30*     (2018.01)

(52) U.S. Cl.
    CPC .............. *G16H 40/67* (2018.01); *G16H 50/20* (2018.01); *G16H 50/30* (2018.01); *G16H 50/50* (2018.01)

(58) Field of Classification Search
    USPC ................ 705/2, 3; 707/722; 706/46, 55, 12
    See application file for complete search history.

(56) References Cited

U.S. PATENT DOCUMENTS

| | | | |
|---|---|---|---|
| 8,560,529 B2 * | 10/2013 | Tunkelang | G06F 16/245 707/722 |
| 8,571,892 B2 | 10/2013 | Averill et al. | |
| 10,380,497 B2 * | 8/2019 | Bhattacharya | G16H 50/20 |
| 2002/0147615 A1 | 10/2002 | Doerr et al. | |
| 2006/0129427 A1 * | 6/2006 | Wennberg | G06F 19/328 705/2 |
| 2010/0145720 A1 * | 6/2010 | Reiner | G06Q 50/2057 705/2 |
| 2014/0012790 A1 * | 1/2014 | Oberkampf | G16H 50/20 706/46 |
| 2015/0242571 A1 | 8/2015 | Naeymi-Rad et al. | |
| 2015/0278457 A1 | 10/2015 | De La Torre et al. | |
| 2015/0356270 A1 | 12/2015 | Devarakonda et al. | |
| 2015/0370979 A1 | 12/2015 | Boloor et al. | |
| 2016/0019361 A1 | 1/2016 | Zasowski et al. | |
| 2017/0140114 A1 * | 5/2017 | Are | G06N 20/00 |

FOREIGN PATENT DOCUMENTS

| | | |
|---|---|---|
| CN | 106682095 A | 5/2017 |
| CN | 106777971 A | 5/2017 |

OTHER PUBLICATIONS

Google patents search, May 28, 2020 (Year: 2020).*
Google patents, Sep. 4, 2020 (Year: 2020).*
ip.com search, Mar. 25, 2021 (Year: 2021).*
The International Search Report and the Written Opinion of the International Searching Authority, or the Declaration, International Appln. No. PCT/IB2018/053845, International Filing Date May 30, 2018, dated Sep. 29, 2018; 10 pps.
Ching-Huei Tsou, et al.; "Toward Generating Domain-Specific / Personalized Problem Lists from Electronic Medical Records"; Cognitive Assistance in Government Papers from the AAAI 2015 Fall Symposium; pp. 66-69.
Lise Poissant, et al.; "Assessing the accuracy of an inter-institutional automated patient-specific health problem list"; Poissant et al. BMC Medical Informatics and Decision Making 2010, 10:10http://www.biomedcentral.com/1472-6947/10/10.
Stephane M. Meystre, et al.; Randomized controlled trial of an automated problem list with improved sensitivity; International journal of medical informatics 77 (2008), pp. 602-612.
Stephane Meystre, et al.; "Natural language processing to extract medical problems from electronic clinical documents: Performance evaluation"; Journal of Biomedical Informatics 39 (2006) 589-599; Department of Medical Informatics, University of Utah School of Medicine, Salt Lake City, UT, USA; Received Jun. 3, 2005.

* cited by examiner

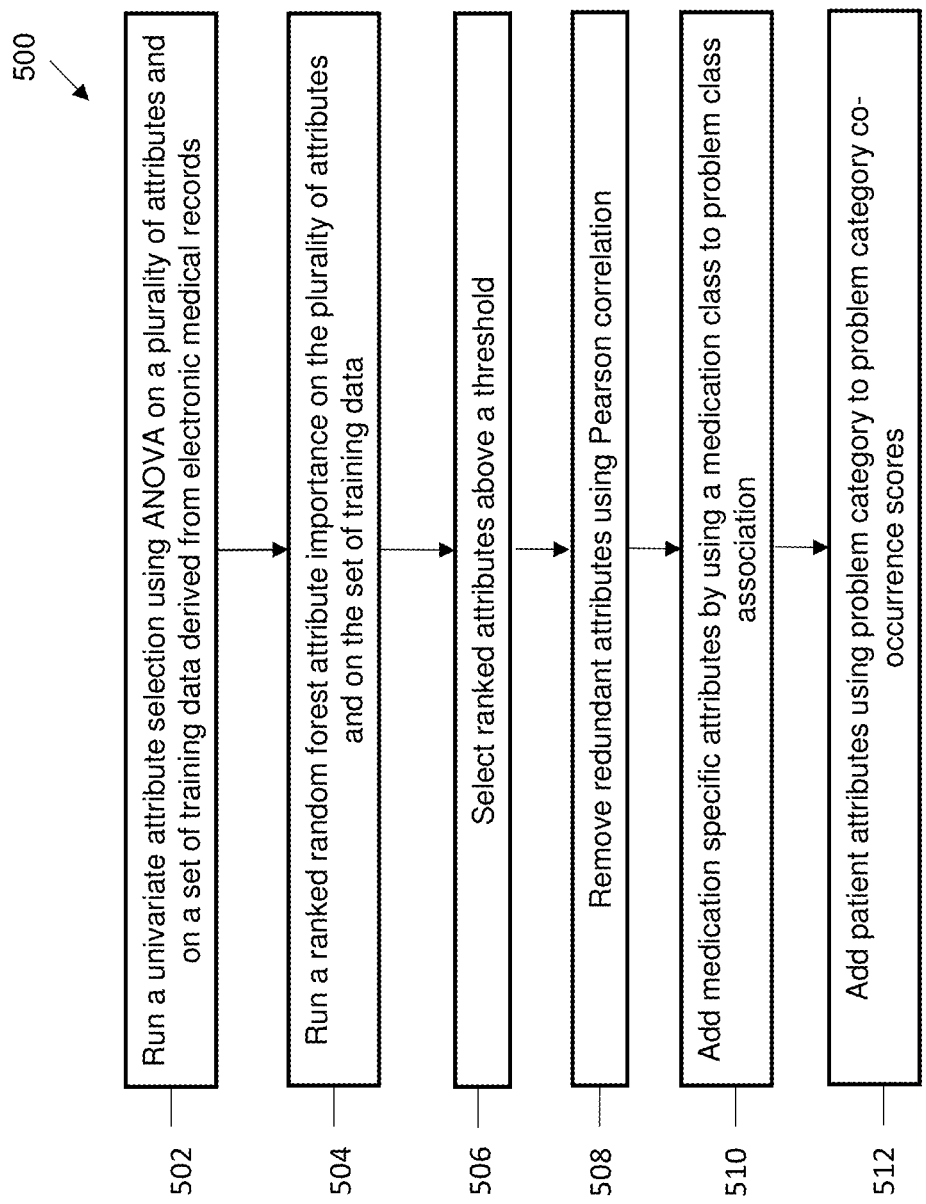

MEDICAL RECORD PROBLEM LIST GENERATION

BACKGROUND

The present invention generally relates to medical records and, more specifically, to automatic medical record problem list generation from electronic medical records.

Current technologies have greatly expanded the type and quantity of patient information that can be collected in connection with medical treatment. An electronic medical record (EMR) stored in an electronic health record (EHR) system includes patient data from a multitude of sources, for a variety of purposes, and in variety of formats. A longitudinal patient record, or an EMR, stored in EHR systems can include hundreds of clinical notes and thousands of semi-structured data entries in addition to structured data entries. Such clinical notes can include not only information intended to be used for patient care, but also information entered for other purposes, such as billing or legal purposes. Thus, although collection of more patient information can be beneficial with respect to patient care, the volume of data collected can make it difficult for patient care providers to comprehend and locate desired or necessary information in a timely manner.

Along with the increased volume of patient data, a patient's medical problem list has become increasingly important in patient treatment and care. Problem lists have been in place for decades and can provide a quick access point for physicians in patient care, can encourage physicians to think holistically about their patients, and can decrease the risk of overlooking medical problems. However, although organizing patient records around problem lists has become a commonly accepted practice, creation and maintenance of accurate and up-to-date problem lists presents a number of challenges. For example, problem lists are not used by every physician, and may or may not be updated. In addition, the level of detail provided in problem lists is not uniform and depends largely upon physician preference.

Recent years have seen research directed to automatic summarization of patient records to reduce a clinician's cognitive load. For example, natural language and machine learning technologies have been used to attempt to summarize, distill and synthesize data from electronic health records. Such methods have met with varied success in the automatic generation of problem lists. However, such methods can suffer from inaccurate measurements and/or limited clinical usefulness. There remains a need for automatic generation of problem lists with improved accuracy from EHRs.

SUMMARY

In accordance with one or more embodiments of the invention, a computer-implemented method for generating a medical problem list is provided. A non-limiting example of the method includes receiving, by a processor, a plurality of disease categories. The method also includes defining, by the processor, a disease category set including a plurality of top level disease categories, wherein the disease category set is based at least in part upon the plurality of disease categories. The method also includes extracting, by the processor, a plurality of candidate training problems from an electronic patient record training set. The method also includes assigning, by the processor, each of the candidate training problems to the plurality of top level disease categories. The method also includes generating, by the processor, a disease category model for each of the top level disease categories from the electronic patient record training set by a machine learning technique. This embodiment of the invention can provide a problem list with improved accuracy and a smaller degree of missed problems or candidate problems that do not reflect medical problems for a patient.

In accordance with one or more embodiments of the invention, a computer program product for generating a medical problem list is provided. The computer program product includes a computer readable storage medium readable by a processing circuit and storing program instructions for execution by the processing circuit for performing a method. A non-limiting example of the method includes receiving a plurality of disease categories. The method also includes defining a disease category set including a plurality of top level disease categories, wherein the disease category set is based at least in part upon the plurality of disease categories. The method also includes extracting a plurality of candidate training problems from an electronic patient record training set. The method also includes assigning each of the candidate training problems to the plurality of top level disease categories. The method also includes generating a disease category model for each of the top level disease categories from the electronic patient record training set by a machine learning technique. This embodiment of the invention can provide a problem list with improved accuracy and a smaller degree of missed problems or problems that do not reflect medical problems for a patient.

In accordance with one or more embodiments of the invention, a processing system for generating a medical problem list includes a processor in communication with one or more types of memory. In a non-limiting example, the processor is configured to receive a plurality of disease categories. The processor is also configured to define a disease category set including a plurality of top level disease categories, wherein the disease category set is based at least in part upon the plurality of disease categories. The processor is also configured to extract a plurality of candidate training problems from an electronic patient record training set. The processor is also configured to assign each of the candidate training problems to the plurality of top level disease categories. The processor is also configured to generate a disease category model for each of the top level disease categories from the electronic patient record training set by a machine learning technique. This embodiment of the invention can provide a problem list with improved accuracy and a smaller degree of missed problems or problems that do not reflect medical problems for a patient.

In accordance with one or more embodiments of the invention, a computer-implemented method for generating a disease category model is provided. A non-limiting example of the method includes receiving, by a processor, a top level disease category. The method also includes extracting, by the processor, a plurality of candidate training problems from an electronic patient record training set. The method also includes assigning, by the processor, each of the candidate training problems to the top level disease category. The method also includes generating, by the processor, a disease category model for the top level disease category based upon the assigned candidate training problems by a machine learning technique. This embodiment of the invention can provide a system for generating a problem list with improved accuracy and a smaller degree of missed problems or candidate problems that do not reflect medical problems for a patient.

In accordance with one or more embodiments of the invention, a processing system for generating a disease category model includes a processor in communication with one or more types of memory. In a non-limiting example, the processor is configured to receive a top level disease category. The processor is also configured to extract a plurality of candidate training problems from an electronic patient record training set. The processor is also configured to assign each of the candidate training problems to the top level disease category. The processor is also configured to generate a disease category model for the top level disease category based upon the assigned candidate training problems by a machine learning technique. This embodiment of the invention can provide a system for creating a problem list with improved accuracy and a smaller degree of missed problems or candidate problems that do not reflect medical problems for a patient.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIG. 9 depicts a flow chart illustrating yet another exemplary method according to one or more embodiments of the present invention.

Figure 1:
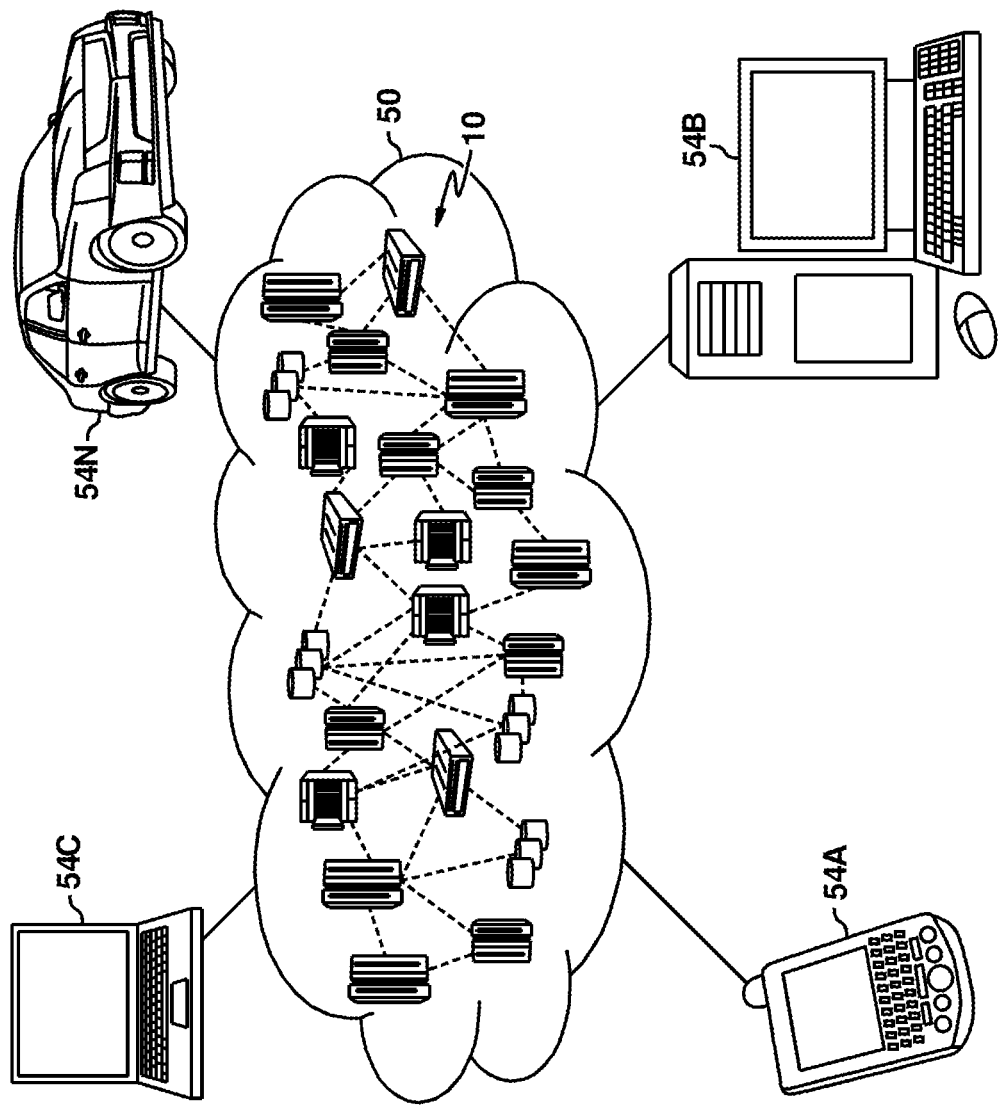
FIG. 1 depicts a cloud computing environment according to an embodiment of the present invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It is understood in advance that although this description includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure including a network of interconnected nodes.

Referring now to FIG. 1, illustrative cloud computing environment 50 according to one or more embodiments of the present invention is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N can communicate. Nodes 10 can communicate with one another. They can be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
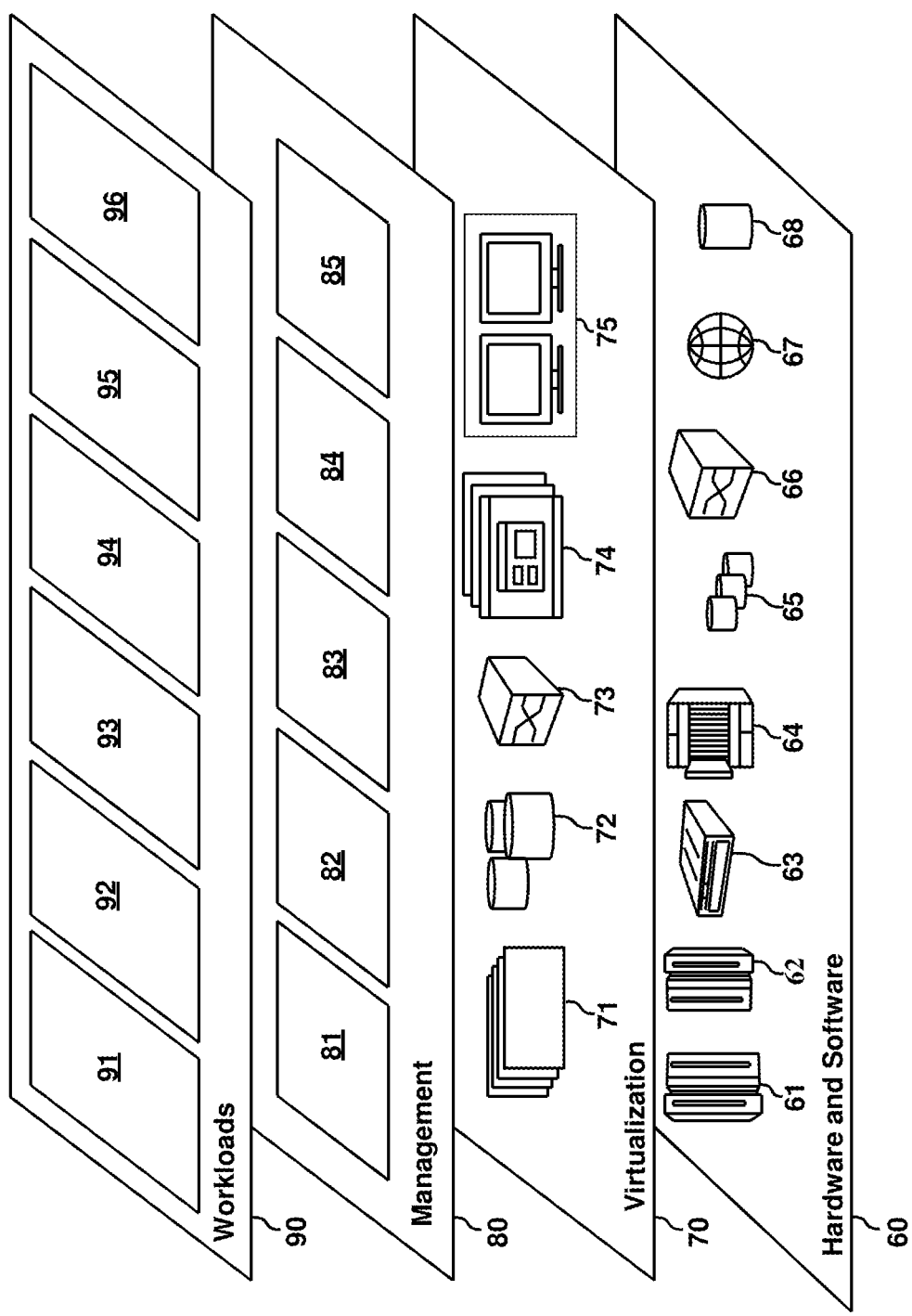
FIG. 2 depicts abstraction model layers according to an embodiment of the present invention.

Referring now to FIG. 2, a set of functional abstraction layers provided by cloud computing environment 50 (FIG. 1) according to one or more embodiments of the present invention is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities can be provided: virtual servers 71; virtual storage 72; virtual networks 73, including virtual private networks; virtual applications and operating systems 74; and virtual clients 75.

In one example, management layer 80 can provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources can include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment can be utilized. Examples of workloads and functions which can be provided from this layer include: mapping and navigation 91; software development and lifecycle management 92; virtual classroom education delivery 93; data analytics processing 94; transaction processing 95; and medical problem list generation 96.

Figure 3:
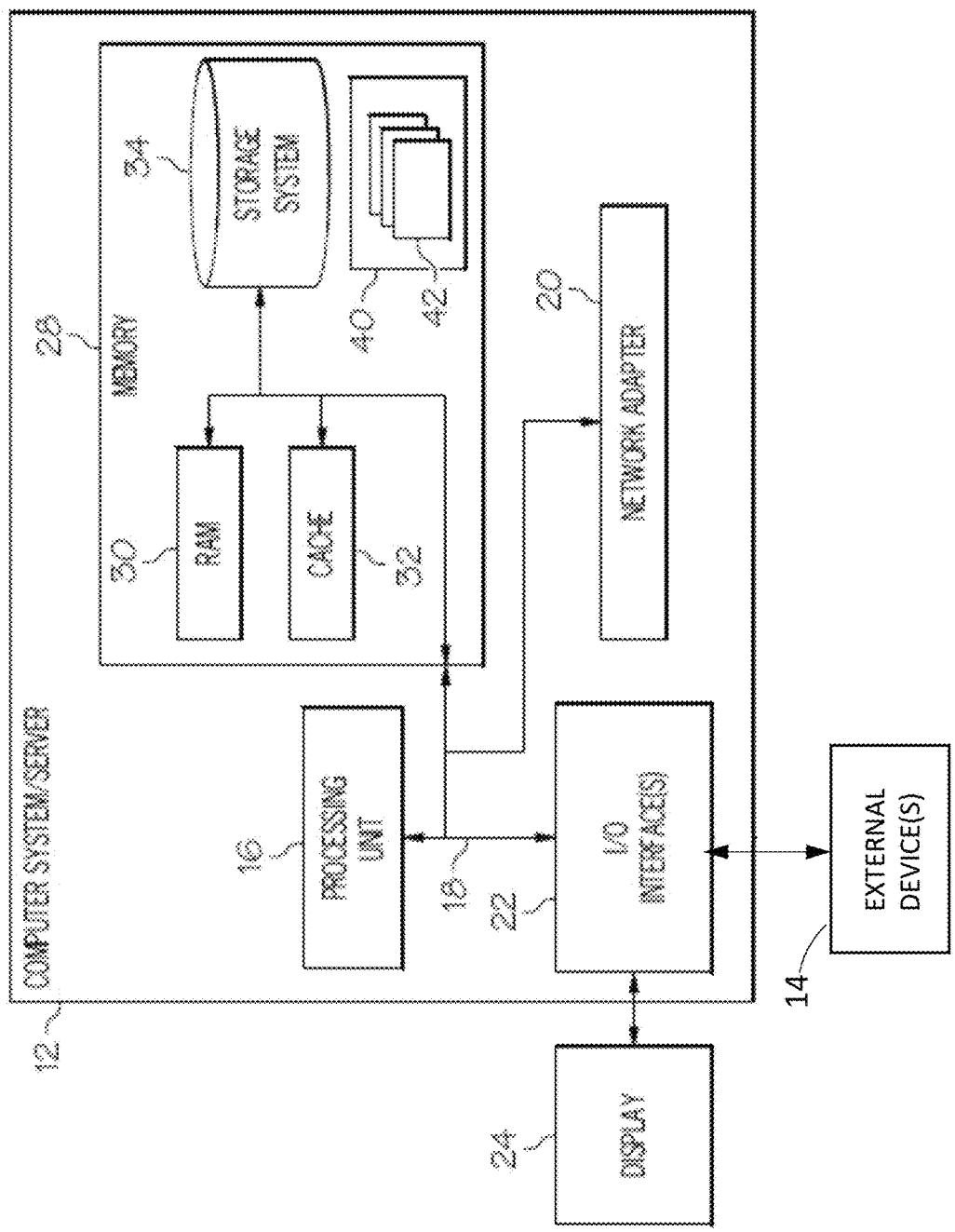
FIG. 3 depicts a computer system according to one or more embodiments of the present invention.

Referring now to FIG. 3, a schematic of a cloud computing node 100 included in a distributed cloud environment or cloud service network is shown according to one or more embodiments of the present invention. The cloud computing node 100 is only one example of a suitable cloud computing node and is not intended to suggest any limitation as to the scope of use or functionality of embodiments of the invention described herein. Regardless, cloud computing node 100 is capable of being implemented and/or performing any of the functionality set forth hereinabove.

In cloud computing node 100 there is a computer system/server 12, which is operational with numerous other general purpose or special purpose computing system environments or configurations. Examples of well-known computing systems, environments, and/or configurations that can be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 can be described in the general context of computer system-executable instructions, such as program modules, being executed by a computer system. Generally, program modules can include routines, programs, objects, components, logic, data structures, and so on that perform particular tasks or implement particular abstract data types. Computer system/server 12 can be practiced in distributed cloud computing environments where tasks are performed by remote processing devices that are linked through a communications network. In a distributed cloud computing environment, program modules can be located in both local and remote computer system storage media including memory storage devices.

As shown in FIG. 3, computer system/server 12 in cloud computing node 100 is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out one or more functions and/or methodologies in accordance with some embodiments of the present invention.

Computer system/server 12 can also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Turning now to an overview of aspects of the invention, embodiments of the present invention provide improved problem lists generated from electronic medical records.

A long standing need in health care is an accurate list of clinical concerns relevant to the care of a patient. Currently, problem lists are frequently generated by administrative or nursing staff of a clinic or hospital. Such lists can be used as a part of a clinical summary of a patient's health record. Electronic problem lists are increasingly relied upon by medical professionals for an overview of patient issues, as the volume of data associated with medical patients increases through digital medical data acquisition and storage. However, problem lists generated in this manner are commonly intended for billing purposes and, therefore, can be highly unreliable and incomplete.

Problem lists with improved accuracy can be generated through analyzing problem specific attributes in addition to problem agnostic attributes and processing such attributes along with extracted candidate problem lists in a plurality of disease-specific learning models. The disease-specific learning models can be automatically generated, in some embodiments of the invention, with a modified alternating decision tree algorithm. Through the use of problem specific attributes and the application of disease-specific models, problem lists with a higher accuracy of identified medical problems can be generated. In some embodiments of the invention, building individual models for each of a defined set of disease categories can achieve higher accuracy not only for that category of diseases, but also for a patient with regard to the entire patient record. As used herein, "medical problems" is understood to mean medical determinations relevant to a patient's quality of life and/or the monitoring and management of which by a medical professional can be beneficial to a patient's health. Exemplary medical problems include chronic diseases that affect the patient's quality of life, differential diagnoses that have not been ruled out, risk factors identified in family history, unresolved medical diagnoses, active medical diagnoses, and the like. Embodiments of the invention include systems trained with information from medical experts that includes ground-truth examples, including examples that specify for a given patient which medical issues and diagnoses would be considered a medical problem and which medical issues and diagnoses would be considered a non-problem.

Figure 4:
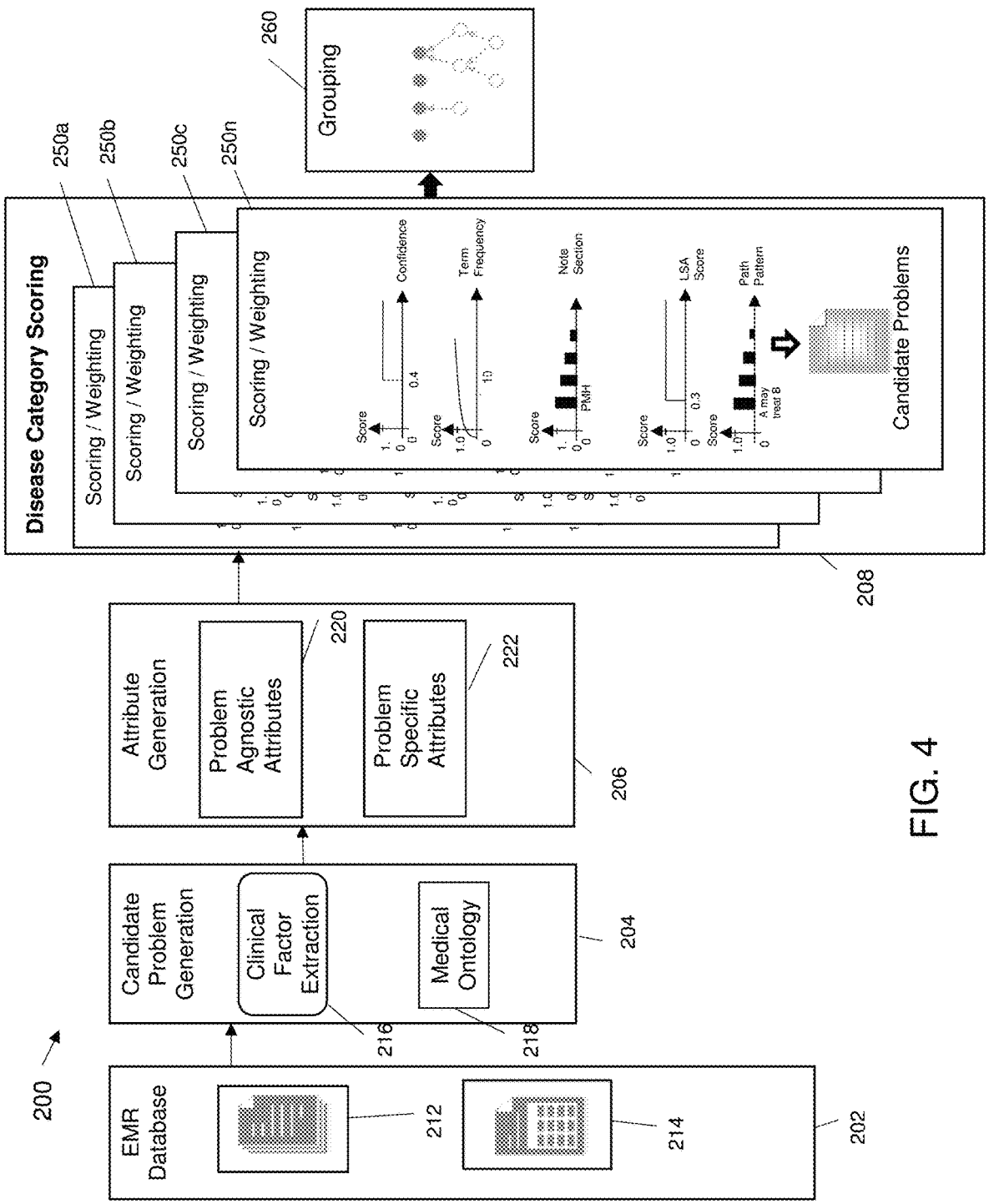
FIG. 4 depicts a diagram illustrating an exemplary system according to one or more embodiments of the present invention.

Turning now to a more detailed description, FIG. 4 depicts an exemplary system 200 for medical record problem list generation according to one or more embodiments of the present invention. The exemplary system 200 includes an EMR database 202. The EMR database 202 can include electronic medical records, including structured data 214 and unstructured and/or semi-structured data 212. The EMR database 202 can communicate with a candidate generation module 204.

In some embodiments of the invention, the candidate problem generation module 204 generates candidate medical problems. Candidate medical problems can include medical problems, resolved medical issues or determinations and unresolved medical issues or determinations that a medical professional would not actively manage or monitor in the course of providing medical care to a patient. The candidate problem generation module 204 can include a clinical factors extraction engine 216, which extracts medical concepts from the EMR database 202, including both from the structured data 214 and the unstructured and/or semi-structured data 212. The clinical factors extraction engine 216 can extract medical concepts from the EMR database by known techniques, such as using natural language processing (NLP). The medical concept extraction, in some embodiments of the invention, can be followed by either a rule-based or learning-based model to classify or map the extracted concepts to candidate medical problems in a medical ontology 218. In some embodiments of the invention, the medical ontology 218 can be included in the candidate problem generation module 204. In some embodiments of the invention, not shown, the medical ontology 218 is external to the candidate generation module 204.

Medical ontologies are known and can be established, defined, catalogued, or maintained by one or more medical standards organizations and the candidate problem generation module can include any medical ontology or dictionary of standardized medical concepts, whether currently known or developed in the future, stored locally, or accessed via a wireless or wired connection in an external system. In some embodiments of the invention, the medical ontology 218 includes a plurality of concept unique identifiers (CUIs) 218. As used herein, "CUIs" include standardized terms that provide an agreed upon or accepted semantic terminology to identify a medically-related issue, such as a medical problem, medical disorder, medication, laboratory result, and the like. The UMLS, for example, includes over 20,000 CUIs. Another exemplary source of CUIs that can be used in embodiments of the invention includes, but is not limited to, the systematized nomenclature of medical codes (SNOMED codes), which can be obtained through the National Library of Medicine's Unified Medical Language Systems UMLS Metathesaurus. In some embodiments of the invention, a candidate medical problem is classified in accordance with a known CUI throughout processing. Exemplary candidate medical problems can include CUIs of unique disorders, medications, laboratory results, etc.

For example, in some embodiments, a medical ontology such as the UMLS is applied to the structured and unstructured data in an electronic medical record to identify medical terminology and classify the candidate medical terminology with the appropriate CUI. A candidate medical problem can include, for instance, a CUI of a unique disorder, medication, or laboratory result.

The exemplary system 200 for medical record problem list generation can also include an attribute generation module 206. The attribute generation module 242 can communicate with the candidate generation module 204 and can receive a plurality of candidate medical problems derived from an EMR database. For each candidate medical problem, the attribute generation module 242 can generate one or more attributes and corresponding attribute scores. In some embodiments of the invention, attributes generated in the attribute generation module 206 include problem agnostic attributes 242 and problem specific attributes 242. Such attributes and attribute scores can be generated by applying a number of known techniques, such as information extraction, text segmentation, and relationship identification. Information extraction, for instance, can include a CUI recognition confidence and a term frequency. Text segmentation, for example, can involve identification of sections within clinical notes and where the candidate medical problems appear within those sections. Text segmentation methods can, for example, identify a non-numeric attribute, such as a name of a section. Relationship identification techniques can perform a latent semantic analysis to identify a relationship between a candidate medical problem and medications, lab test results, and the like. Problem agnostic attributes 220 and problem specific attributes 222 can this include, for instance: lexical attributes, incorporating standard information retrieval measures such as term frequency and inverse document frequency; medical attributes, describing relationships between candidate medical problems and medications, procedures, and laboratory test results; frequency attributes, capturing the prior probability of a medical problem, for instance in connection with the usage field in SNOMED CORE; structural attributes, including for instance a note type and section type where a candidate problem is mentioned; and temporal attributes, describing a distribution of different candidate problems mentioned in patient's electronic medical record; and higher-order combinations of the aforementioned attributes. With the exception of higher-order combinations of the aforementioned attributes, most of the aforementioned attributes include problem agnostic attributes 220.

Problem specific attributes 222 can include higher order attributes, which can be generated by combining one or more attributes. For example, a term frequency attribute can be correlated with assertion type, note type, note section type, and a moving window in a temporal dimension to generate a plurality of higher order attributes. An exemplary resultant higher order attribute can include the "number of times hypertension is mentioned as positive in the assessment and plan section in a progress note in the last three months." Such problem specific attributes 222 can better capture the complexity of the data generation process.

In some embodiments of the invention, the attribute generation module 206 reduces the dimensionality of attributes generated. For example, generation of higher order attributes can grow the number of attributes substantially, such as from 234 to millions of attributes. Thus, using a large number of such combined attributes can, in some cases, over-fit a data set. In some embodiments of the invention, dimension reduction is beneficial to mitigate issues pertaining to over-fitting of data sets. The dimensionality of attributes can be reduced by known techniques. For example, auto-encoders can be used to reduce dimensionality and learn a general representation of a medical problem that captures hierarchical dependencies of the starting attributes. An auto-encoder is an unsupervised attribute construction technique that can use a neural network structure to reproduce its own input as output to learn a distributed representation of starting attributes. In some embodiments of the invention, de-noising auto-encoders are used to reduce the dimensionality of attributes. For example, de-noising auto-encoders can learn a robust representation of attributes from a noisy input. In some embodiments of the invention, a plurality of stacked auto-encoders built into a deep auto-encoder are used to reduce the dimensionality of attributes.

In some embodiments, the system 200 includes a disease category scoring module 208. The disease category scoring module 208 can include a set of disease category templates 250a, 250b, 250c, . . . 250n. In some embodiments of the invention, the disease category templates in the set each represent a top level category from a disease category classification list. In some embodiments, the disease category classification list includes a single tree hierarchy, such as classification lists from the International Statistical Classification of Diseases and Related Health Problems, including for instance International Classification of Diseases revision 9, (ICD-9), or ICD-10. All or part of a disease category classification list can be used in the set of disease category templates. For example, in an embodiment using top level categories from ICD-9, the following set of disease category models can be used: 1. symptoms, signs, and ill-defined conditions; 2. diseases of the skin and subcutaneous tissue; 3. diseases of the genitourinary system; 4. infectious and parasitic diseases; 5. diseases of the respiratory system; 6. neoplasms; 7. diseases of the musculoskeletal system and connective tissue; 8. endocrine, nutritional & metabolic diseases; 9. diseases of the circulatory system; 10. congenital anomalies; 11. diseases of the nervous system; 12. diseases of the sense organs; 13. diseases of the digestive system, 14. injury and poisoning; 15. diseases of the blood & blood forming organs; 16. mental disorders; 17. other. In this embodiment, the category "other" includes problems to which an ICD-9 code cannot readily or automatically be assigned to an ICD-9 code and top-level ICD-9 categories that contain insignificant numbers of samples or numbers of samples below a designated threshold, which include in this example "external injury and supplement classification," "certain conditions originating in the prenatal period," and "complication of pregnancy, child birth and puerperium."

In some embodiments of the invention, the disease category scoring module 208 creates a set of disease category models 250a . . . 250n by employing a training phase, in which a plurality of candidate problems are extracted from an electronic patient record training set and assigned to a top level disease category from a disease category set, such as a set derived from ICD-9 codes. Machine learning can be used to generate the disease category modules. In some embodiments, a separate machine learning model is used for each of the disease categories. In some embodiments, the disease category scoring module 208 automatically identifies useful attributes for each of the disease category models from a large set of attributes. As used herein, "useful attributes" includes a set of attributes that represent the attributes statistically determined to be the most useful for distinguishing between a candidate problem that is a medical problem and a candidate problem that is not a medical problem.

In some embodiments of the invention, the disease category scoring module 206 generates an attribute score for each attribute. Attribute scores can be generated using multiple scoring processes, the choice of which can depend upon the nature of the attribute. Attribute scores can represent a numerical or non-numerical attribute such as, for example, a frequency of the attribute, an importance of the attribute, a percentage relative to acceptable standards, quantity of medication, medication strength, longevity of use of a medication. In some embodiments, attributes are categorized before scoring processes are applied, and the type scoring processes applied to each attribute can vary based upon the attribute category. In some embodiments, the choice of attribute scoring processes depends at least in part upon the disease category model. For example, each disease category model can have an associated set of attribute scoring processes that can be the same or different from the other disease category models in the set.

In some embodiments of the invention, each disease category model 250a . . . 250n of the disease category scoring module 208 can normalize, filter, and weight each attribute using its associated attribute score to provide a final combined attribute score for each candidate medical problem. The weighting of each attribute can be determined using machine learning techniques.

Each of the aforementioned techniques, processes, and system components that uses machine learning techniques can dynamically change over time. For example, but not by weigh of limitation, the weighting of attributes can dynamically change over time as the machine learning processes refine the best weighting parameters to reflect a likelihood that candidate medical problems classified by standardized medical concepts are medical problems of patients associated with electronic medical records. For example, a machine learning process can dynamically increase the weighting of attribute scores based upon the locations of candidate medical problem attributes within the structure of medical records. By way of another example, a machine learning process can dynamically increase or decrease the weighting of attribute scores based upon how recently a candidate medical problem attributes appear within the electronic medical records in response to feedback and use empirical texting and modeling. Thus, in some embodiments of the invention, processes and models can dynamically evolve to more accurately match candidate medical problems classified by CUIs to medical problems of patients.

The system 200 for medical record problem list generation can also include a grouping module 260. In some embodiments of the invention, the grouping module 260 receives scored medical problems from each of the disease category models. In some embodiments of the invention, the grouping module 260 can merge and cluster closely related problems based upon a known medical problem classification hierarchy. For example, a problem list resulting from a combined list of problems generated in each disease specific model can be grouped in the grouping module 206 based on clinical similarities of the problems. For example, diabetes mellitus and diabetes type II can be grouped into a single problem for the purpose of making a concise medical problem list because one is a specific form of the other. In some embodiments, for example and not by way of limitation, the grouping module 260 uses UMLS provided "isa" relationships and clustering techniques from known art based on characteristics of the problem such as the body part affected, medications used in treatment, and the like. Many other UMLS relationships can be used for clustering closely related medical concepts and would readily be known and/or recognized by persons of ordinary skill in the art.

The grouping module 260 can apply filters to the scored medical problems such that candidate medical problems having criterial below a certain threshold are not included in a final medical problem list. For example, if a final combined attribute score for a candidate medical problem corresponding to a candidate medical problem is below a threshold, that candidate medical problem can be filtered out. The filtering threshold can be manually set or automatically adjusted, for instance to increase or decrease a total number of medical problems included in a medical problem list, to change a volume of results output, or to achieve other purposes desired by the user. In some embodiments of the invention, after grouping and filtering, the grouping module generates a medical problem list. In some embodiments of the invention, the grouping module performs a plurality of iterations using, in each iteration, only the highest scoring or weighted medical problems resulting from the previous iteration.

Figure 6:
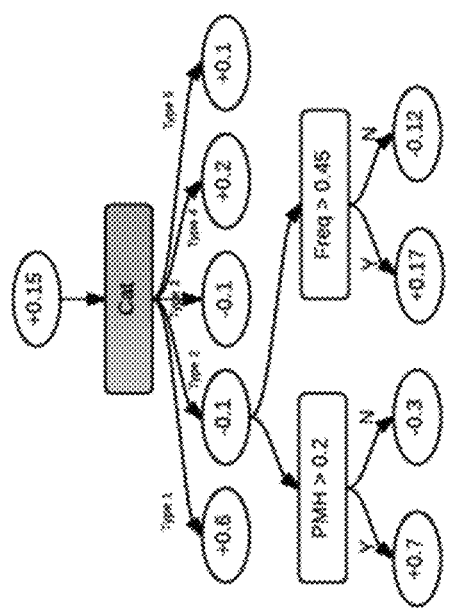
FIG. 6 depicts another exemplary tree generated from a categorical attribute with multiple possible categories according to one or more embodiments of the present invention.
Figure 5:
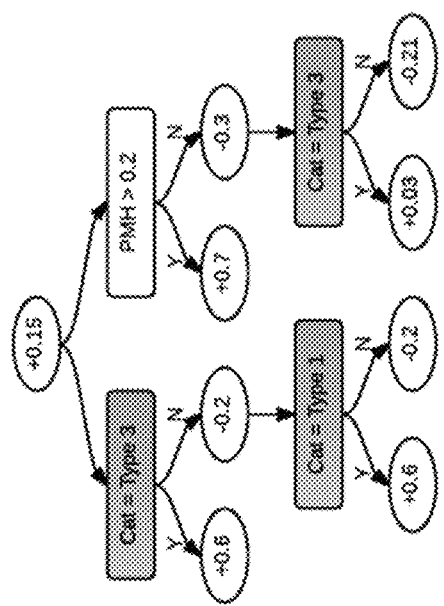
FIG. 5 depicts an exemplary tree generated from a categorical attribute with multiple possible categories according to one or more embodiments of the present invention.

In some embodiments, disease category models $250a \ldots 250n$ can be generated through a modified alternating decision tree (ADT) algorithm. In some embodiments, problem specific attributes 222 are selected within each disease category using unsupervised attribute selection. For example, problem specific attributes 222 can be selected by stratifying a plurality of training attributes into categories and then performing embedded, supervised attribute selection within each category through a modified ADT algorithm. An ADT alternates between two nodes, a prediction node and a splitter node. Unlike in a decision tree, in an ADT, an instance can travel through multiple paths and a prediction is made by the sign of the sum of all prediction node values along the paths. Each decision node in an ADT is a binary classifier. To generate disease category specific models automatically, a multi-class splitter node can be included in an ADT to generate a modified ADT. The multi-class splitter node can classify each instance into one of the possible categories. For example, a splitter node can have a rule of the following form:

if (precondition = true) then
 switch (condition)
  case $c_i$: return $a_i$
 else return 0 where $c_i$ is one of the possible disease categories and $a_i$ is the prediction value in the prediction node, calculated using $$a_i = 1/2 \ln\left(\frac{W_+(p \wedge c_i)+1}{W_-(p \wedge c_i)+1}\right)$$

where $W_+(.)$ and $W_-(.)$ are the summation of the weights of each positive and negative training example, respectively, that satisfies the precondition and condition. For each iteration step t, the categorical splitter note has a training error $Z_t$, $$Z_t(p, C) = 2\left(\sum_{c_i \in C} \sqrt{W_+(p \wedge c_i)W_-(p \wedge c_i)}\right) + W(\neg p)$$

where p is the preconditions at step t, C is the categorical condition, and $c_i$ is a valid category in C. FIG. 5 depicts an exemplary tree generated from a categorical attribute with multiple possible categories using a conventional ADT. FIG. 6 depicts an exemplary tree generated from the same categorical attribute from the modified ADT. As is shown in FIGS. 5 and 6, using a conventional ADT, the same attribute can be chosen more than once and performs a binary split each time it is selected, whereas using a modified ADT, a categorical attribute performs a multiclass split that generates one prediction node for each category. In some embodiments, a prior weight can be assigned to a categorical attribute when calculating a training error to guide the model to stratify data early in the learning process.

Figure 7:
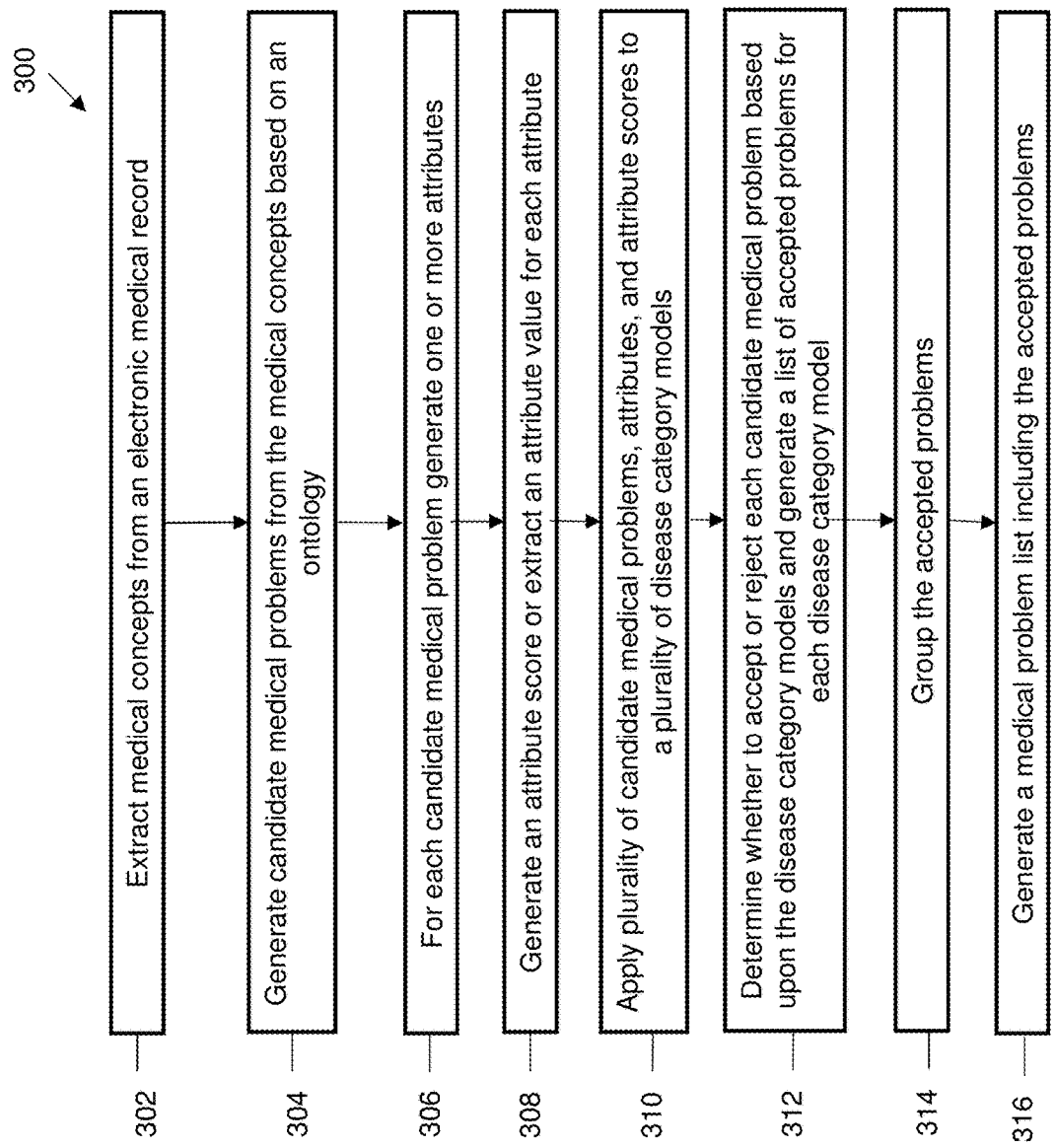
FIG. 7 depicts a flow chart illustrating an exemplary method according to one or more embodiments of the present invention.

FIG. 7 depicts a flow chart illustrating an exemplary method 300 for generating a medical problem list according to one or more embodiments of the present invention. The method 300 includes extracting medical concepts from an electronic medical record as shown in block 302. The method 300 also includes generating candidate medical problems from the medical concepts based on an ontology as shown in block 304. The method 300 also includes, for each candidate medical problem, generating one or more attributes as shown in block 306. The method 300 also includes generating an attribute score or extracting an attribute value for each attribute as shown in block 308. The method 300 also includes applying the plurality of candidate problems, attributes, and attribute scores to a plurality of disease category models as shown in block 310. The method 300 also includes determining whether to accept or reject each candidate medical problem based upon the disease category model as shown in block 312. The method 300 also includes grouping the accepted problems as shown in block 314. The method 300 also includes generating a medical problem list including the accepted problems as shown in block 316.

Figure 8:
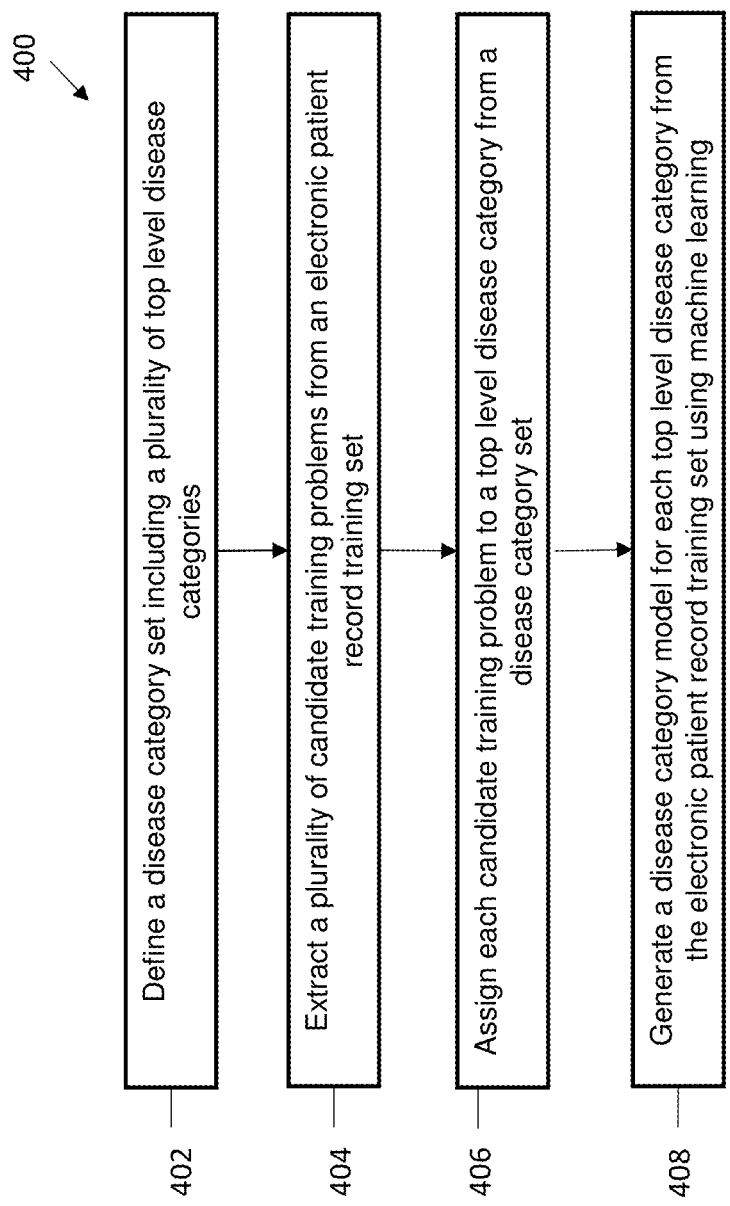
FIG. 8 depicts a flow chart illustrating another exemplary method according to one or more embodiments of the present invention.

FIG. 8 depicts a flow chart illustrating an exemplary method 400 for generating a set of disease category models according to one or more embodiments of the present invention. The method 400 includes defining a disease category set including a plurality of top level disease categories as shown in block 402. The method 400 also includes extracting a plurality of candidate training problems from an electronic patient record training set as shown at block 404. The method 400 also includes assigning each candidate training problem to a top level disease category from a disease category set as shown in block 406. The method 400 also includes generating a disease category model for each top level disease category from the electronic patient record training set using machine learning as shown at block 408.

FIG. 9 depicts a flow chart illustrating an exemplary method 500 for identifying useful attributes for each of the disease category models according to one or more embodiments of the present invention. The exemplary method 500 includes running a univariate attribute selection using ANOVA on a plurality of attributes and on a set of training data derived from electronic medical records, as shown at block 502. The method 500 also includes, as shown at block 506, selecting ranked attributes above a threshold. The method 500 also includes, as shown at block 508, removing redundant attributes using Pearson correlation. The method 500 also includes, as shown at block 510, adding medication specific attributes by using a medication class to problem class association. The method 500 also includes adding patient attributes using problem category to problem category co-occurrence scores, as shown at block 512.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form described. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There can be many variations to this diagram or the steps (or operations) described therein without departing from the spirit of embodiments of the invention. For instance, the steps can be performed in a differing order or steps can be added, deleted or modified. All of these variations are considered a part of the claimed invention.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A non-transitory computer program product for generating a medical problem list, the computer program product comprising:
    a computer readable storage medium readable by a processing circuit and storing program instructions for execution by the processing circuit for performing a method comprising:
    receiving a plurality of disease categories;
    defining a disease category set comprising a plurality of top level disease categories selected from a disease category classification list, the disease category classification list comprising a single tree hierarchy;
    extracting a plurality of candidate training problems from an electronic patient record training set according to an ontology;
    assigning each of the candidate training problems to the plurality of top level disease categories;
    generating a plurality of disease category templates, wherein each disease category template represents one top level disease category of the plurality of top level disease categories;
    generating a unique disease category model for each disease category template from the electronic patient record training set by a machine learning technique, wherein each of the disease category models identifies, for the respective top level disease category, a set of attributes statistically determined to distinguish between a candidate problem that is a medical problem and a candidate problem that is not a medical problem; and
    wherein each disease category model is generated through a modified alternating decision tree (ADT) configured such that a categorical attribute performs a multiclass split that generates one prediction node for each category.

2. The computer program product of claim 1, wherein the method further comprises applying an electronic patient data set to the disease category model for each of the top level disease categories to generate a plurality of scored candidate medical problems.

3. The computer program product of claim 2, wherein the method further comprises generating a medical problem list based at least in part upon the scored candidate medical problems.

4. The computer program product of claim 3, wherein the electronic patient data set comprises a plurality of candidate medical problems and a plurality of attributes associated with each candidate medical problem.

5. The computer program product of claim 4, wherein at least some of the attributes are problem-specific attributes.

6. The computer program product of claim 1, wherein the machine learning technique comprises stratifying a plurality of training attributes into a plurality of categories.

7. The computer program product of claim 2, wherein the method further comprises filtering the scored candidate medical problems to remove all candidate medical problems having a score below a threshold from a candidate problem list.

8. A processing system for generating a medical problem list, comprising:
a processor in communication with one or more types of memory, the processor configured to:
receive a plurality of disease categories;
define a disease category set comprising a plurality of top level disease categories selected from a disease category classification list, the disease category classification list comprising a single tree hierarchy;
extract a plurality of candidate training problems from an electronic patient record training set according to an ontology;
assign each of the candidate training problems to the plurality of top level disease categories;
generate a plurality of disease category templates, wherein each disease category template represents one top level disease category of the plurality of top level disease categories;
generate a unique disease category model for each disease category template from the electronic patient record training set by a machine learning technique, wherein each of the disease category models identifies, for the respective top level disease category, a set of attributes statistically determined to distinguish between a candidate problem that is a medical problem and a candidate problem that is not a medical problem; and
wherein each disease category model is generated through a modified alternating decision tree (ADT) configured such that a categorical attribute performs a multiclass split that generates one prediction node for each category.

9. The processing system of claim 8, wherein the method further comprises applying an electronic patient data set to the disease category model for each of the top level disease categories to generate a plurality of scored candidate medical problems.

10. The processing system of claim 9, wherein the method further comprises generating a medical problem list based at least in part upon the scored candidate medical problems.

11. The processing system of claim 9, wherein the electronic patient data set comprises a plurality of candidate medical problems and an attribute associated with each candidate medical problem.

12. The processing system of claim 11, wherein the attribute includes a problem-specific attribute.

13. The processing system of claim 8, wherein the machine learning technique comprises stratifying a plurality of training attributes into a plurality of categories.

* * * * *